United States Patent [19]

Whisson

[11] Patent Number: 5,759,177
[45] Date of Patent: Jun. 2, 1998

[54] INJECTION DEVICE WHICH IS RENDERED UNUSABLE ON THE COMPLETION OF ITS USE

[75] Inventor: Maxwell Edmund Whisson, Perth, Australia

[73] Assignee: Eastland Technology Australia Pty Ltd, Wangara, Australia

[21] Appl. No.: 809,757

[22] PCT Filed: Sep. 14, 1995

[86] PCT No.: PCT/AU95/00604

§ 371 Date: Mar. 13, 1997

§ 102(e) Date: Mar. 13, 1997

[87] PCT Pub. No.: WO96/08283

PCT Pub. Date: Mar. 21, 1996

[30] Foreign Application Priority Data

Sep. 16, 1994 [AU] Australia ................. PM8294

[51] Int. Cl.[6] ........................................... A61M 5/32
[52] U.S. Cl. ........................................... 604/195; 604/110
[58] Field of Search .................................. 604/195, 110, 604/198, 187, 218, 220, 137, 138, 89

[56] References Cited

U.S. PATENT DOCUMENTS

| | | |
|---|---|---|
| 4,908,022 | 3/1990 | Haber . |
| 5,120,310 | 6/1992 | Shaw . |
| 5,188,613 | 2/1993 | Shaw .................... 604/195 |
| 5,562,635 | 10/1996 | Whisson .................... 604/195 |

FOREIGN PATENT DOCUMENTS

| | | |
|---|---|---|
| 0 326 983 | 8/1989 | European Pat. Off. . |
| 9320872 | 10/1993 | WIPO . |

*Primary Examiner*—Michael Buiz
*Assistant Examiner*—Kevin Truong
*Attorney, Agent, or Firm*—Merchant, Gould, Smith, Edell, Welter & Schmidt

[57] ABSTRACT

An injection device comprising a hollow body (11) having a forward end (12) and a rearward end (13), the forward end (12) slidably receiving a hollow needle (15), the body (11) providing a chamber (A) between its forward end (12) and its rearward end (13), the chamber being defined between a plug (17) and a stop (18), the plug (17) being sealingly and slidably received within the body (11) adjacent the forward end (12), the stop (18) being slidably and sealingly received within the body (11) rearward of the plug (17) wherein a greater degree of effort must be applied to the stop (18) than to the plug (17) to effect slidable movement within the body, the rearward end (13) of the body having a portion (14) in which the stop (18) is not sealingly received within the body, a drive element (19) connected at one end to the plug (17) and slidingly and sealingly received through the stop (18) to extend from the rearward end (13) of the body (11), a manipulation member (20) provided on the other end of the drive element (19), the hollow interior of said needle (15) being connected to the chamber (A) through a flexible passageway (21) extending between the inner end of the needle (15) and the plug (17), the needle (15) being connected to the plug (17).

20 Claims, 2 Drawing Sheets

INJECTION DEVICE WHICH IS RENDERED UNUSABLE ON THE COMPLETION OF ITS USE

BACKGROUND OF THE INVENTION

1. Field of the Invention

THIS INVENTION relates to an injection device and in particular relates to a device in the form of a syringe which can be utilised for the injection of a parenteral agent into the body.

2. Description of the Related Art

The present invention comprises a development beyond the device disclosed in International patent application PCT/AU93/00175 and International patent application PCT/AU94/00618, the contents of each of which are included herein by reference. Each of those disclosures relate to injection devices which can be utilised in the injection of a parenteral agent into the body whereby on completion of the injection, the device is rendered unusable. It is a characteristic of each of these devices, however, that during the injection of the parenteral agent the needle is moved rearwardly within the body of the syringe, and as a result of that movement, the tip of the needle is caused to move outwardly from tissue within which it may be located. While this arrangement may be satisfactory in a large number of applications, there are instances in which it is necessary to deposit the parenteral agent deeply within the tissue and/or where retraction of the needle within the body during the injection process is undesirable.

SUMMARY OF THE INVENTION

It is an object of this invention to provide an injection device which is capable of being rendered unusable on completion of its use, but which is arranged such that the needle can remain substantially generally stationery within the tissue during the injection step.

In one form, the invention resides in an injection device comprising a hollow body, having a forward end and a rearward end, the forward end slidably receiving a hollow needle, the body providing a chamber between its forward end and its rearward end, the chamber being defined between a plug and a stop, the plug being sealingly and slidably received within the body adjacent the forward end, the stop being slidably and sealingly received within the body rearward of the plug wherein a greater degree of effort must be applied to the stop than to the plug to effect slidable movement within the body, the rearward end of the body having a portion in which the stop is not sealingly received in the body, a drive element connected at one end to the plug member and slidingly and sealingly received through the stop member to extend from the rearward end of the body, a manipulation means provided on the other end of the drive element, the hollow interior of said needle being connected to the chamber through a flexible passageway extending between the inner end of the needle and the plug, said needle being connected to the plug or stop by a tensioning means, a means between the needle and body adapted to retain the needle at a first position at which it extends from the body and said means being adapted to be able to release the needle to allow the needle to move to a second position at which it is accommodated within the body, the movement between the first and second position being effected by the tensioning means.

According to a preferred feature of the invention, the drive element is flexible. It is a preferred characteristic of the drive element that the manipulation means cannot be used to push the stop or the plug towards the forward end of the body. The manipulation means may comprise a slider which is slidably supported in the rearward end of the body or alternatively may take the form of a ring or tab or like means which can be grasped and pulled to effect movement of the plug.

According to a further preferred feature of the invention, the rearmost end of the body is configured such that movement of the stop and plug into the rearward end is irreversible.

According to a preferred feature of the invention, the tensioning means comprises a flexible tube which also forms the passageway. The tube may be formed of a suitable resiliently extendable material and/or a resiliently extendable element may be incorporated into or around the tube. According to further form, the tube may be formed of a rigid material such as metal or a suitable plastics material which is also resilient and where the tube is formed as a spring. The spring may be of the coiled form or may be of a form which in its relaxed state has the shape of a spiral and which when stretched has the shape of a cone.

According to a further preferred feature of the invention, the means comprises a frictional engagement between the inner end of the needle and the body whereby the means will release the needle on the tensioning means providing a predetermined force to the needle. The needle can be supported from a boss or like member which is slidably received by the internal wall of the body.

According to a further alternative feature of the invention the means may comprise a latch or like engagement means which can positively engage the needle or its support when in the first position, where the means can be disengaged from the needle to permit it to move to the second position.

BRIEF DESCRIPTION OF THE DRAWING

The invention will be more fully understood in the light of the following description of one specific embodiment. The description is made with reference to the accompanying drawings of which.

DESCRIPTION OF THE PREFERRED EMBODIMENT

Figure 1:
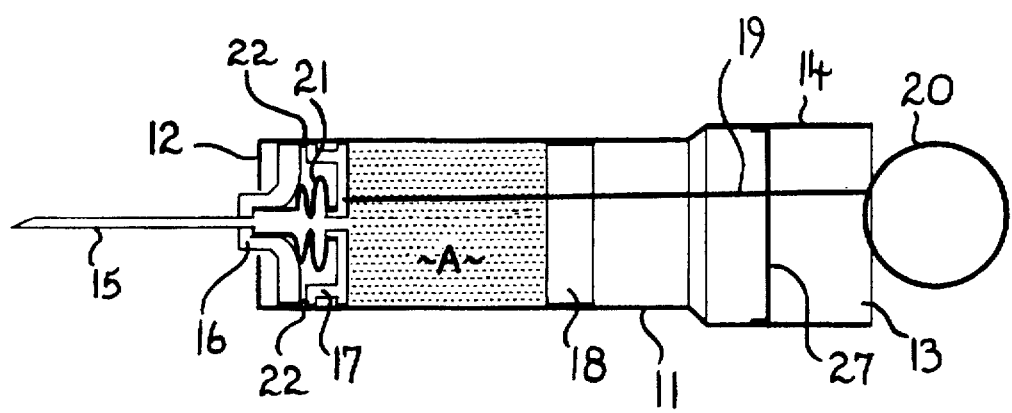
FIG. 1 is a schematic sectional elevation of the embodiment prior to injection.
Figure 2:
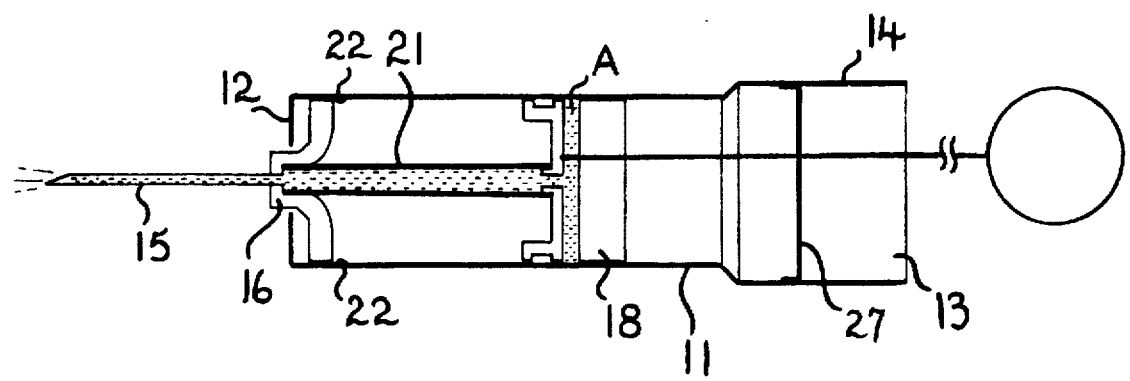
FIG. 2 is a schematic sectional elevation of the embodiment at the completion of injection.
Figure 3:
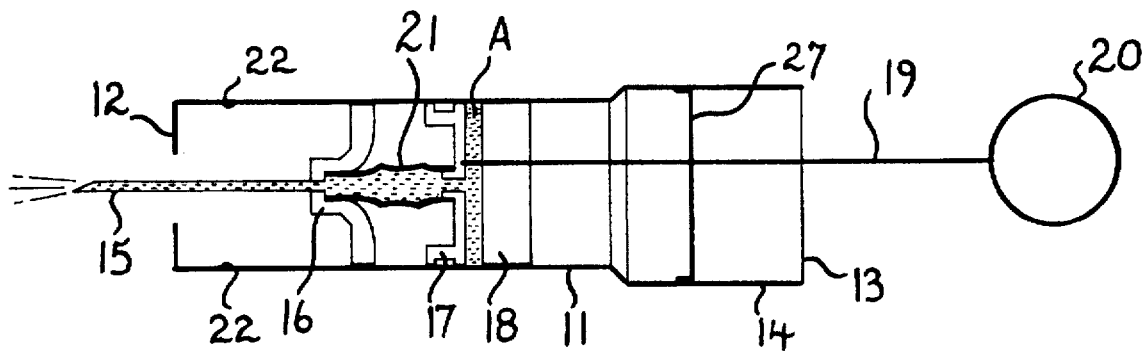
FIG. 3 is a sectional elevation of the embodiment illustrating retraction of the needle at an intermediate position.

The embodiment comprises an injection device of the form disclosed in PCT/AU93/00175 and PCT/AU94/00618 and which comprises a syringe having substantially hollow cylindrical body 11 having a forward end 12 and a rearward end 13. The rearward portion 14 of the embodiment adjacent the rear end 13 is formed with an increased diameter. The body 11 supports a hollow needle 15 which is supported from a boss element 16 which is slidingly received within the body 11.

The body 11 provides a chamber A which is defined between a plug member 17 and a stop member 18 which are each slidingly and sealingly received within the body 11. The slidable engagement of the stop member 18 and plug member 17 is such that a greater degree of force is required to effect slidable movement of the stop member 18 within the body than to effect slidable movement of the plug member 17 within the body.

The plug member 17 is connected to a drive element in the form of an elongate flexible element 19 that may take the form of a thread or wire or the like, and which is fixed at one end to the plug 17. The flexible element 19 is slidably and sealingly received through the stop member 18 and is provided at its free end with a manipulation means 20 which can take the form of a ring as shown, or a tab, or a slider which is slidably supported by the rearward end portion of the body as disclosed in PCT/AU94/00618.

The interior of the hollow needle 15 is connected to the chamber A through a flexible tube 21 which extends between the boss 16 and the plug 17. The flexible tube is also formed to be resiliently extensible.

The boss 16 is frictionally engaged with the interior walls of the body 11 such that when the needle 15 is in its extended position, an increased amount of force is required to displace the boss 16 from that position, and whereby on being displaced from the position the boss 16 will move relatively freely within the body 11. The increased frictional engagement is effected by the provision of a protrusion 22 on the inner surface of the body 11 at its forward end which is engaged by the boss 16 when the needle 15 is in its extended position. As an alternative the boss 16 may be frictionally engaged with the opening provided in the forward end 12 in a manner which will enable the needle 15 to be released on a sufficient force being applied by the tensioning means. In such an instance the boss 16 will need to be provided with a stabilising means which will support the boss 16 to enable it to remain substantially central as it moves rearwardly through the body towards the rearward end.

The boss 16 is not sealingly engaged with the internal wall of the body 11 in order to permit the escape of air from between the boss 16 and the plug 17 as the boss 16 moves towards the plug 17 under the influence of the tensioning means.

The rearward portion of the body 11 is provided with a barrier means 27 which prevents the plug 17 being pulled from the body 11.

The embodiment takes the form of a prefilled syringe in which the needle occupies the first position at which it is extended as shown at FIG. 1, and where the parenteral agent is accommodated within the chamber A between the plug member 17 and the stop member 18. In utilisation of the syringe, the needle 15 is located in the tissue of the patient and by pulling on the manipulation means 20, the plug 17 is moved rearwardly within the body 11 towards the stop 18. Because of the differential frictional engagement between the plug member 17 and the walls of the body 11 as compared with the frictional engagement of the stop member 18 with the walls of the body 11, as the plug 17 is moved towards the stop 18, the latter remains in position, causing the chamber A to reduce in volume. As a result the parenteral agent is ejected from the chamber A through the flexible tube 21 into the hollow needle 15 and then into the tissue in which the needle 15 is located.

Figure 4:
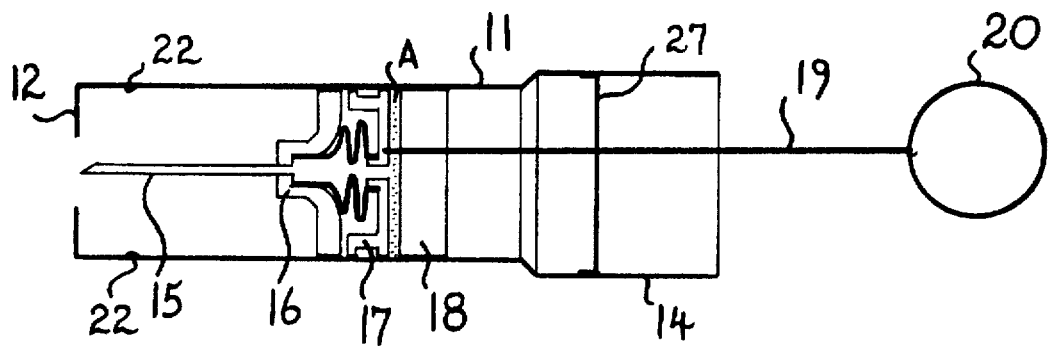
FIG. 4 is a sectional elevation of the invention embodiment illustrating the needle in the fully retracted position against the stop prior to retraction of the stop.

As the plug member 17 is displaced, the flexible tube 21 is caused to become resiliently elongated and is tensioned. This tension increases as the plug member 17 moves towards the stop member 18. As the plug member 17 approaches the stop member 18, the force applied to the boss element 16 by the tensioned flexible tube 21 becomes sufficient to overcome the frictional engagement forces retaining the boss element 16 in its forwardmost position. Once the boss element 16 becomes disengaged from its forwardmost position it is pulled towards the plug 17 under the influence of the tensioned flexible tube 21 until it is closely adjacent the stop 18. At that position the needle is fully retracted to lie within the body as shown at FIG. 4.

Figure 5:
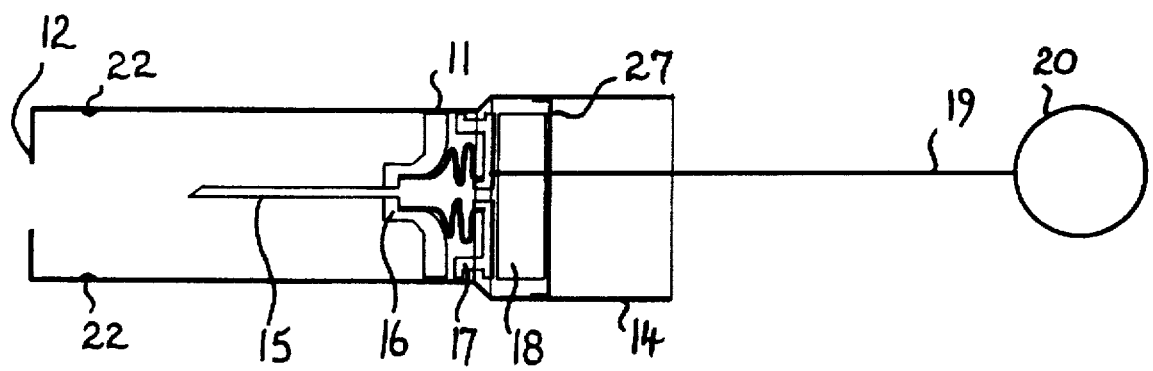
FIG. 5 is a sectional elevation of the embodiment illustrating the needle and stop in the fully retracted position.

On completion of the movement of the plug 17 towards the stop 18 the plug 17 will become engaged with the stop 18. Further retraction by the manipulation means will cause the stop 18 to enter the enlarged rearward portion 14 of the body 11 at which position the stop will become sealingly disengaged from the walls of the chamber A. As shown at FIG. 5, the rearward portion 14 may be dimensioned such that the plug 17, and possibly the boss 16, may also be drawn into the rearward portion 14, where the plug 17 will become sealingly disengaged from the walls of the body 11.

If desired the rearward portion of the body may be formed of a differing cross-section from the forwardmost portion or with a groove or slot in order that the sealing engagement of the stop with the internal wall of the body is broken and that the chamber A ceases to be a sealed chamber.

It should be appreciated that the scope of the present invention not be limited to the particular scope of the embodiment described above.

I claim:

1. An injection device comprising:
    a hollow body having a forward end and a rearward end;
    a hollow needle slidably received in the forward end, the body providing a chamber between its forward end and its rearward end, the chamber being defined between a plug and a stop, the plug being sealingly and slidably received within the body adjacent the forward end, the stop being slidably and sealingly received in the body rearward of the plug and intermediate of the forward end and rearward end, wherein a greater degree of effort must be applied to the stop than to the plug to effect slidable movement within the body, the rearward end of the body having a portion which is adapted to receive the stop in non-sealing engagement;
    an elongate drive element having one end connected to the plug, the drive element being slidingly and sealingly received through the stop to extend from the rearward end of the body;
    a manipulation means provided on another end of the drive element;
    a hollow interior of said needle being connected to the chamber through a flexible passageway extending between an inner end of the needle and the plug, said needle being connected to the plug by a tensioning means; and
    a retaining means between the needle and body for retaining the needle at a first position at which it extends from the body and for releasing the needle to allow the needle to move to a second position at which it is accommodated within the body, the movement between the first and second position being effected by the tensioning means.

2. An injection device as claimed at claim 1 wherein the drive element is flexible.

3. A injection device as claimed at claim 2 wherein the manipulation means comprises a tab.

4. An injection device as claimed at claim 2 wherein the manipulation means comprises a slider slidably supported in the rearward portion of the body.

5. An injection device as claimed at claim 4, wherein the drive means comprises a filament.

6. An injection device as claimed at claim 5, wherein the rearward end of the body is configured such that with movement of the plug into the rearward end portion, the stop is also capable of movement into the rearward portion.

7. An injection device as claimed at claim 6, wherein the retaining means comprises a frictional engagement between the needle and the body whereby the needle will become disengaged from said frictional engagement on the tensioning means providing a predetermined force to the needle.

8. An injection device as claimed at claim 7, wherein the retaining means comprises a latch which can positively engage the needle when in the first position and whereby the latch can be disengaged from the needle to permit the needle to move to the second position under the influence of the tensioning means.

9. An injection device as claimed at claim 8, wherein the means comprises flexible tube which also forms the passageway.

10. An injection device as claimed in claim 2 wherein the manipulation means comprises a ring.

11. An injection device as claimed at claim 1 wherein the drive means comprises a filament.

12. An injection device as claimed at claim 1 wherein the rearward end of the body is configured such that with movement of the plug into the rearward end portion, the stop is also capable of movement into the rearward portion.

13. An injection device as claimed at claim 12 wherein an internal face of the body is configured such that movement of the plug and/or stop into the rearward portion is irreversible.

14. An injection device as claimed at claim 1 wherein the retaining means comprises a frictional engagement between the needle and the body whereby the needle will become disengaged from said frictional engagement on the tensioning means providing a predetermined force to the needle.

15. An injection device as claimed at claim 14 wherein the inner end of the needle is supported from the body by a support member which is frictionally engaged with the body.

16. An injection device as claimed at claim 1 wherein the retaining means comprises a latch which can positively engage the needle when in the first position and whereby the latch can be disengaged from the needle to permit the needle to move to the second position under the influence of the tensioning means.

17. An injection device as claimed at claim 1 wherein the tensioning means comprises flexible tube which also forms the passageway.

18. An injection device as claimed at claim 17 wherein the tube is formed of a resiliently extendable material.

19. An injection device as claimed at claim 17 wherein the flexible tube comprises a tubular member having a resiliently extendible member incorporated into or around walls of the tube.

20. An injection device as claimed at claim 17 wherein the tube is formed of a rigid material which is resilient and which has the form of a coiled or spiral spring.

* * * * *